(12) United States Patent
Shin

(10) Patent No.: US 12,105,885 B2
(45) Date of Patent: Oct. 1, 2024

(54) TOUCH CONTROL OF WEARABLE DEVICES

(71) Applicant: GOOGLE LLC, Mountain View, CA (US)

(72) Inventor: Dongeek Shin, Santa Clara, CA (US)

(73) Assignee: GOOGLE LLC, Mountain View, CA (US)

( * ) Notice: Subject to any disclaimer, the term of this patent is extended or adjusted under 35 U.S.C. 154(b) by 0 days.

(21) Appl. No.: 18/006,096

(22) PCT Filed: Sep. 27, 2021

(86) PCT No.: PCT/US2021/071602
§ 371 (c)(1),
(2) Date: Mar. 30, 2023

(87) PCT Pub. No.: WO2023/048753
PCT Pub. Date: Mar. 30, 2023

(65) Prior Publication Data
US 2023/0418386 A1    Dec. 28, 2023

(51) Int. Cl.
*G06F 3/01*    (2006.01)
*G04G 21/02*    (2010.01)
(Continued)

(52) U.S. Cl.
CPC .......... *G06F 3/017* (2013.01); *G04G 21/025* (2013.01); *G04G 21/08* (2013.01); *G06F 3/0304* (2013.01)

(58) Field of Classification Search
CPC ..... G04G 21/025; G04G 21/08; G06F 3/0304
See application file for complete search history.

(56) References Cited

U.S. PATENT DOCUMENTS 8,634,836 B2    1/2014    Pani et al.
11,051,706 B1    7/2021    Nadeau et al.
(Continued)

FOREIGN PATENT DOCUMENTS

JP    2016115310 A    6/2016
JP    2017530443 A    10/2017
(Continued)

OTHER PUBLICATIONS

International Search Report and Written Opinion for PCT Application No. PCT/US2021/071602, mailed on May 27, 2022, 15 pages.
(Continued)

*Primary Examiner* — Kenneth B Lee, Jr.
(74) *Attorney, Agent, or Firm* — Brake Hughes Bellermann LLP

(57) ABSTRACT

A sensor on a wearable device may be further configured as a sensor for detecting and recognizing a gesture to control the wearable device. For example, light detected by a photoplethysmography (PPG) sensor of a smart watch may include (i) light back reflected from underneath the smart watch and (ii) light back reflected from a touch to a wrist adjacent to the smart watch. The detected light may be filtered to isolate the light back reflected from the touch. A waterfall image that includes information about how the isolated light changes with time and amplitude may be generated and used to detect and recognize gestures performed on the wrist, such as a touch. This additional touch area may help to supplement a touch area provided by a display to control the smart watch.

19 Claims, 13 Drawing Sheets

(51) Int. Cl.
    *G04G 21/08*     (2010.01)
    *G06F 3/03*     (2006.01)

(56) References Cited

U.S. PATENT DOCUMENTS

| | | | |
|---|---|---|---|
| 2017/0060242 A1* | 3/2017 | Gill | G02B 5/1871 |
| 2017/0075426 A1* | 3/2017 | Camacho Perez | G06F 1/163 |
| 2018/0317770 A1* | 11/2018 | Ortega | G06F 3/011 |
| 2020/0150772 A1 | 5/2020 | Quinn et al. | |
| 2021/0280322 A1* | 9/2021 | Frank | G16H 50/20 |
| 2022/0300082 A1* | 9/2022 | Shin | G01S 7/417 |

FOREIGN PATENT DOCUMENTS

| | | |
|---|---|---|
| JP | 2019032891 A | 2/2019 |
| KR | 20150009360 A | 1/2015 |

OTHER PUBLICATIONS

Yadav, "On Establishing PPG Biometrics for Human Recognition: Feasibility and Variability", Jul. 2018. 94 pages.
Zhang, et al., "Motion Artifact Reduction for Wrist-Worn Photoplethysmograph Sensors Based on Different Wavelengths", Sensors, 19, 673; (www.mdpi.com/ournal/sensors), 2019, 18 pages.
Zhao, et al., "PPG-Based Finger-Level Gesture Recognition Leveraing Wearables", IEEE INFOCOM 2018—IEEE Conference on Computer Communications, Apr. 16, 2018, 9 pages.

\* cited by examiner

TOUCH CONTROL OF WEARABLE DEVICES

CROSS REFERENCE TO RELATED APPLICATION

This application is a 35 U.S.C. § 371 National Phase Entry Application from PCT/US2021/071602, filed Sep. 27, 2021, designating the U.S., the disclosure of which is incorporated herein by reference in its entirety.

FIELD OF THE DISCLOSURE

The present disclosure relates to wearable devices and more specifically to a smart watch that can respond to a touch to the user in areas adjacent to the smart watch.

BACKGROUND

Wearable devices, such as smart watches, may have touch screen displays that enable a user to interact with the device using touch gestures, such as a click, a double click, or a scroll. Touch screens are often sized comparable to a wrist of the user, and it is not uncommon for a touch screen to have a dimension of less than 2 inches (i.e., <50 millimeters). This size can limit what is displayed for touch interaction. For example, a total number of icons simultaneously displayed on the touch screen of a smart watch may be limited so that the size of each icon remains large enough for a user to conveniently touch. Increasing a touch area by physically expanding the touch screen or limiting what is displayed on the screen at any given time may not be desirable to a user. Accordingly, the functionality of the smart watch can be limited by the area provided for touch interaction.

SUMMARY

In at least one aspect, the present disclosure generally describes a method for controlling a wearable device. The method includes receiving light at a detector on the wearable device, where the received light includes a focused-light component and a stray-light component. The method further includes filtering the received light to isolate the stray-light component and generating a waterfall image of the stray-light component. The waterfall image has pixel values corresponding to amplitudes of the stray-light component measured (at intervals) during a window of time. The method further includes analyzing the waterfall image to detect a touch and identifying a gesture in the waterfall image using a gesture classifier when the touch is detected. The method further includes controlling the wearable device based on the gesture.

The waterfall image may be a two-dimensional image that represents possible amplitudes (i.e., intensities) of the stray-light component measured at intervals (i.e., time samples) during the window of time. Accordingly, the pixels of the waterfall image may have pixel values that represent the amplitudes of the stray-light component at times within the window. The process to generate the waterfall image can thus include gathering time samples continuously, and a sliding window may select a set of the time samples for a waterfall image. A collection (i.e., set) of time sampled amplitudes is then converted to a waterfall image. Converting the detector data into a waterfall image may advantageously allow for image processing techniques to be used to determine a touch. Detecting a touch based on the waterfall image may relate to detecting a touch event or an indication of a touch based on pixel values of the generated waterfall image. A touch in this context may for example relate to a touch of a body part, in particular a skin surface. Such a touch may affect the amplitudes of the stray-light component. The stray-light component may result from a focused-light reflected by a finger or hand of a user touching the body part.

Identifying a gesture in response to detecting a touch, may generally comprise analyzing the waterfall image for a presence of pixel values in the waterfall image indicative of a gesture. In this context, the method may take into account that different types of gestures and/or different gestures result in different waterfall images respectively characteristic for a type of gesture or a certain gesture. The gesture classifier may for example be configured to recognize a pattern in the waterfall image corresponding to the gesture. In a possible implementation, the gesture classifier may be configured to recognize different types of gestures on the basis of different types of stored (and previously learned) reference patterns corresponding to the different types of gestures.

In a possible implementation of the method, filtering the received light to isolate the stray-light component includes performing principal component analysis on the received light to isolate the stray-light component.

In another possible implementation of the method, analyzing the waterfall image to detect the touch includes determining order statistics of the waterfall image and applying the order statistics to a touch classifier to obtain a touch probability. The order statistics may include a maximum pixel value and a minimum pixel value and applying the order statistics to the touch classifier may include determining whether a touch (event) is present in the generated waterfall image or not based on applying a probability function using the maximum pixel value and the minimum pixel value for the waterfall image.

Based on the touch probability, the analysis can, in a possible implementation, further include determining that a touch has occurred during the window of time or that a touch has not occurred during the window of time. The touch or not touch determination may trigger a further process. For example, when no touch has occurred (and thus a touch (event) was not detected based on the waterfall image) the gesture classifier is not used to identify the gesture in the waterfall image in order to conserve power.

In another possible implementation of the method, the order statistics of the waterfall image include a maximum pixel value and a minimum pixel value, and the touch classifier comprises a support vector machine configured to return a touch probability based on the maximum pixel value and the minimum pixel value.

In another possible implementation of the method, the gesture classifier comprises (in particular may be) a two-dimensional (2D) convolutional neural network and/or is configured to recognize a pattern in the waterfall image corresponding to the gesture. In particular the gesture classifier may be configured to recognize different types of gestures on the basis of different types of stored reference patterns corresponding to the different types of gestures. Accordingly, different touch gestures may each have a characteristic waterfall image.

In a first possible implementation, the gesture classifier is configured to recognize a single bright spot in the waterfall image as a single-click gesture.

In a second possible implementation, the gesture classifier is configured to recognize two bright spots in the waterfall image as a double-click gesture.

In a third possible implementation, the gesture classifier is configured to recognize a bright stripe extending in time from a higher amplitude of the waterfall image to a lower amplitude of the waterfall image as a scroll-down gesture.

In a fourth possible implementation, the gesture classifier is configured to recognize a bright stripe extending in time from a lower amplitude of the waterfall image to a higher amplitude of the waterfall image as a scroll-up gesture.

In another possible implementation of the method, the wearable device is a smart watch.

In another possible implementation of the method, the detector is part of a photoplethysmography sensor directed towards a wrist of a user, where the photoplethysmography sensor further includes a light source configured to project the light towards the wrist of the user.

In another possible implementation of the method, the light is at a visible wavelength or an infrared wavelength.

In another aspect, the present disclosure generally describes a smart watch. The smart watch includes a sensor, for example a photoplethysmography sensor, that includes a light source and a detector. The light source is configured to project transmitted light including focused-light transmitted towards a portion of a wrist under the smart watch and stray-light transmitted towards a portion of the wrist not under the smart watch. The detector is configured to receive back-reflected light including a focused-light component that is reflected back to the detector from the portion of a wrist under the smart watch and a stray-light component that is reflected back to the detector from the portion of the wrist not under the smart watch. The smart watch further includes at least one processor that is configured by software instructions (i.e., the at least one processor is configured to perform certain actions based on software instructions when the software instructions are executed by the at least one processor). The at least one processor is configured to filter the back-reflected light to isolate the stray-light component. The at least one processor is further configured to generate a first waterfall image of the stray-light component, where the first waterfall image has pixel values corresponding to amplitudes of the stray-light component measured during a first window of time. The at least one processor is further configured to analyze the first waterfall image to detect a touch in the first waterfall image.

In a possible implementation of the smart watch, the at least one processor is further configured to route the first waterfall image to a gesture classifier when a touch is detected in the first waterfall image. The gesture classifier is configured to recognize a pattern in the first waterfall image as a gesture to control the smart watch.

In an implementation of the gesture classifier, the gesture classifier is configured to recognize different types of gestures. For example, the gesture classifier may be configured to recognize a signal bright spot in the first waterfall image as a single-click gesture and recognize two bright spots in the first waterfall image as a double-click gesture. The gesture classifier may be further configured to recognize a bright stripe extending in time from a higher amplitude of the first waterfall image to a lower amplitude of the first waterfall image as a scroll-down gesture and recognize a bright stripe extending in time from the lower amplitude of the first waterfall image to the higher amplitude of the first waterfall image as a scroll-up gesture.

In another possible implementation of the smart watch, the at least one processor is further configured by software to generate a second waterfall image of the stray light component measured during a second window of time and discard the first waterfall image when a touch is not detected in the first waterfall image. The second window of time and the first window of time being iterations of a sliding widow applied to the stray-light component. The at least one processor may then be further configured to analyze the second waterfall image to detect a touch in the second waterfall image.

In another possible implementation of the smart watch, filtering the back-reflected light to isolate the stray-light component includes the at least one processor being configured to perform principal component analysis on the back-reflected light to determine the focused light component and subtract the focused-light component from the back-reflected light to isolate the stray-light component.

In another possible implementation of the smart watch, analyzing the first waterfall image to detect a touch in the first waterfall image includes the at least one processor being configured to classify the first waterfall image as having a touch or not having a touch based on a maximum pixel value of the first waterfall image.

In another aspect, the present disclosure generally describes a smart watch that includes a sensor and at least one processor. The sensor includes a light source that is configured to project transmitted light towards a portion of a wrist adjacent to the smart watch and a detector configured to receive back-reflected light from the portion of the wrist adjacent to the smart watch. The at least one processor is configured by software instructions to generate a waterfall image of the back-reflected light, where the waterfall image has pixel values that correspond to amplitudes of the back-reflected light measured during a first window of time. The at least one processor is further configured by software instructions to analyze the waterfall image to detect a touch to the portion of the wrist not under the smart watch. The at least one processor is further configured to identify a pattern in the waterfall image as a gesture when the touch is detected and control the smart watch based on the gesture.

In a possible implementation of the smart watch, the at least one processor is further configured by software instructions to filter the back-reflected light to make the touch (event) visible in the waterfall image.

In another possible implementation of the smart watch, controlling the smart watch based on the gesture includes controlling a device coupled to the smart watch.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The components in the drawings are not necessarily to scale relative to each other. Like reference numerals designate corresponding parts throughout the several views.

DETAILED DESCRIPTION

Figure 1:
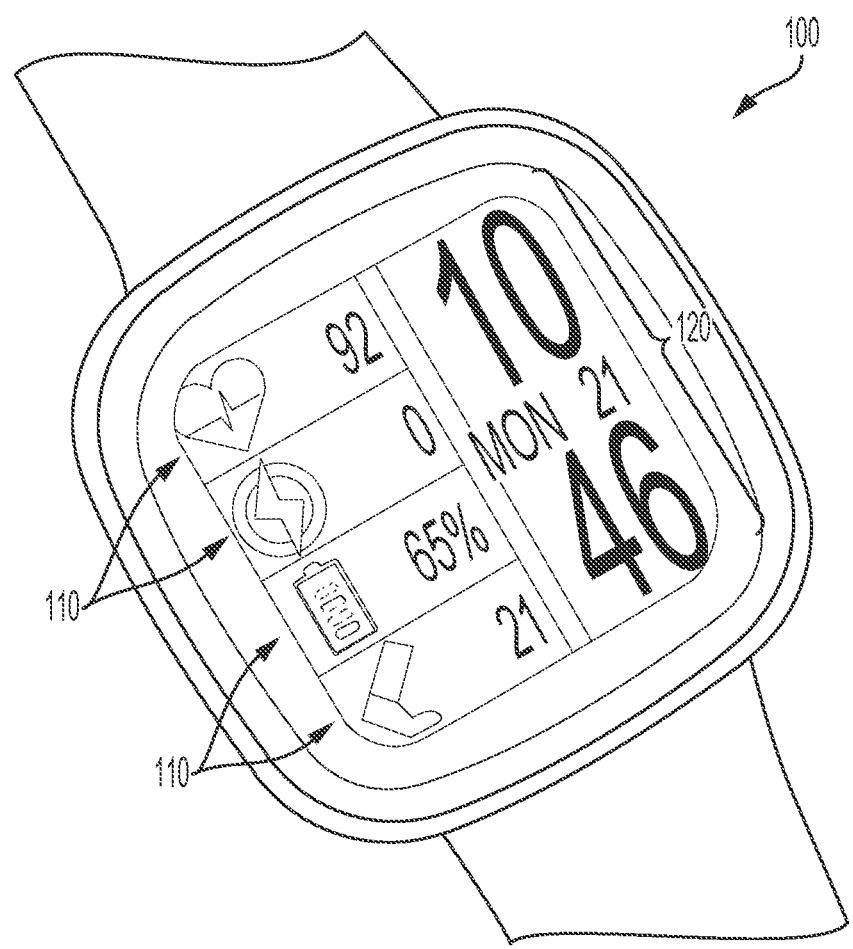
FIG. 1 illustrates a top view of a smart watch according to a possible implementation of the present disclosure.

The functionality of a wearable device (e.g., smart watch, fitness tracker) can be limited by a screen area necessary for touch interaction. FIG. 1 illustrates a top view of a smart watch 100 according to a possible implementation of the present disclosure. As shown in FIG. 1, when multiple icons 110 are displayed on a touch screen 120, a touch area for each icon may be a small portion of the touch screen 120. Accordingly, the amount of information and how it is displayed can be constrained when touch interaction is required. Limiting touch function when information content is increased is a technical problem with wearable devices, such as the smart watch 100. Increasing the size of the touch display to address this technical problem may not be desirable from a fashion and/or wearability standpoint and adding touch function via new sensors/electronics could drain a power/processing budget for these devices and could increase their cost.

The disclosed circuits and methods address this technical problem by extending the area for touch interaction to a wrist of a user. For example, a touch interaction with the smart watch may be initiated and completed on the skin of the user adjacent to the smart watch (e.g., on the wrist or hand) without requiring a touch interaction with the smart watch itself. The disclosed solution advantageously provides the added touch functionality using sensors/electronics that may already exist on the smart watch. Accordingly, the added touch functionality provided by the disclosed technology does not necessarily increase complexity, cost, or power consumption of an existing smart watch. Further, in some implementations, the disclosed solution may be provided to existing smart watches without a hardware change (e.g., via a software update) so that these devices can utilize a new type of touch interaction. The new type of touch interaction may have the technical effect of enabling the smart watch to display more information and may change how a user interacts with the device. These technical effects may facilitate how/what information is displayed on the smart watch and may enable new applications for the smart watch.

Figure 2:
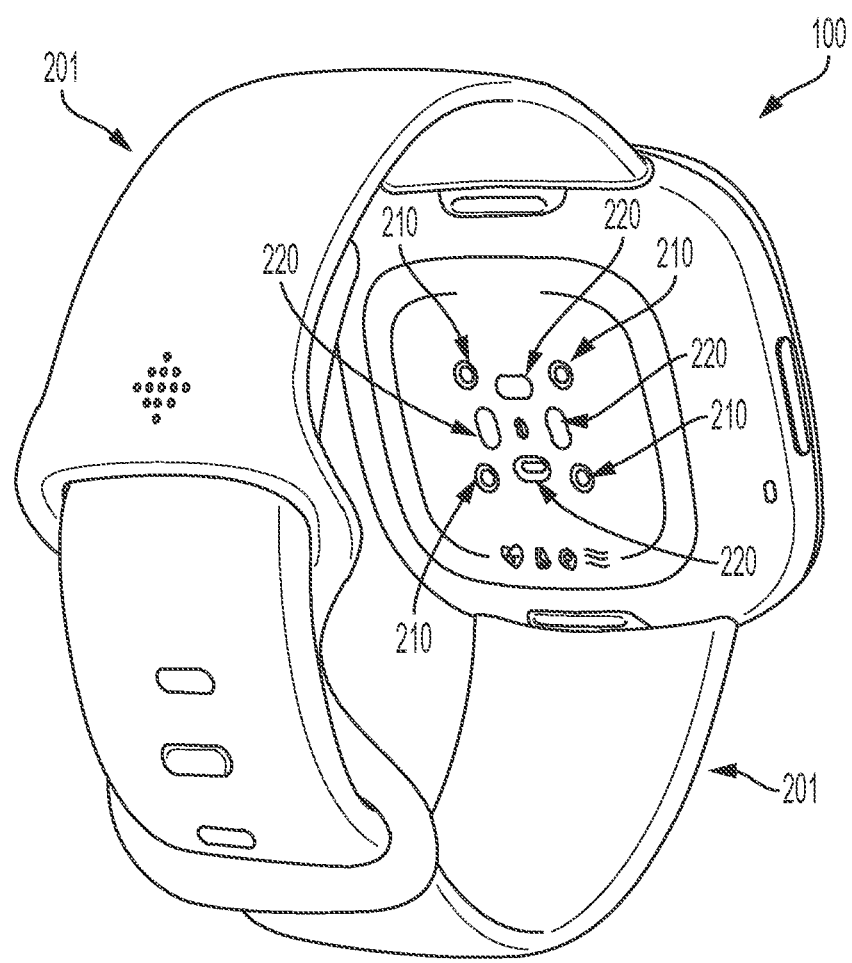
FIG. 2 illustrates a bottom view of the smart watch shown in FIG. 1.

FIG. 2 illustrates a bottom view of the smart watch shown in FIG. 1. The smart watch 100 includes straps 201 that are configurable to hold a bottom surface of the smart watch to a wrist of a user. The bottom surface of the smart watch includes a photoplethysmography (PPG) sensor that can be configured to measure a heart rate of a user (i.e., wearer). The PPG sensor includes one or more illuminators (e.g., LEDs 210) and one or more detectors (e.g., photodiodes 220). The LEDs 210 can be configured to transmit focused light towards a user's wrist. The transmitted light may include wavelengths in the visible portion of the spectrum (e.g., 530 nanometer (green)) for increased resolution (i.e., visible wavelength) and/or wavelengths in the infrared portion of the spectrum (e.g., 730 nanometer (nm)) for increased skin penetration (i.e., infrared wavelength). For example, the wavelength may be in a near infrared (NIR) portion of the section.

The transmitted light can penetrate the skin of the user to illuminate blood vessels of the user. Blood in the blood vessels can reflect (i.e., back-reflect) light towards the photodiodes 220. The photodiodes 220 are directed to the wrist of the user to measure an intensity of the back-reflected light. The intensity of the back-reflected light is modulated as the volume of the blood in the blood vessels change. Accordingly, signals from the photodiodes 220 may be processed (e.g., filtered) and analyzed (e.g., Fourier transformed) to determine a heart rate. The processing may include low-pass filtering of the back-reflected light to obtain frequencies corresponding to the heart rate, which may be in a relatively low frequency band (60-180 beats per minute).

Figure 3:
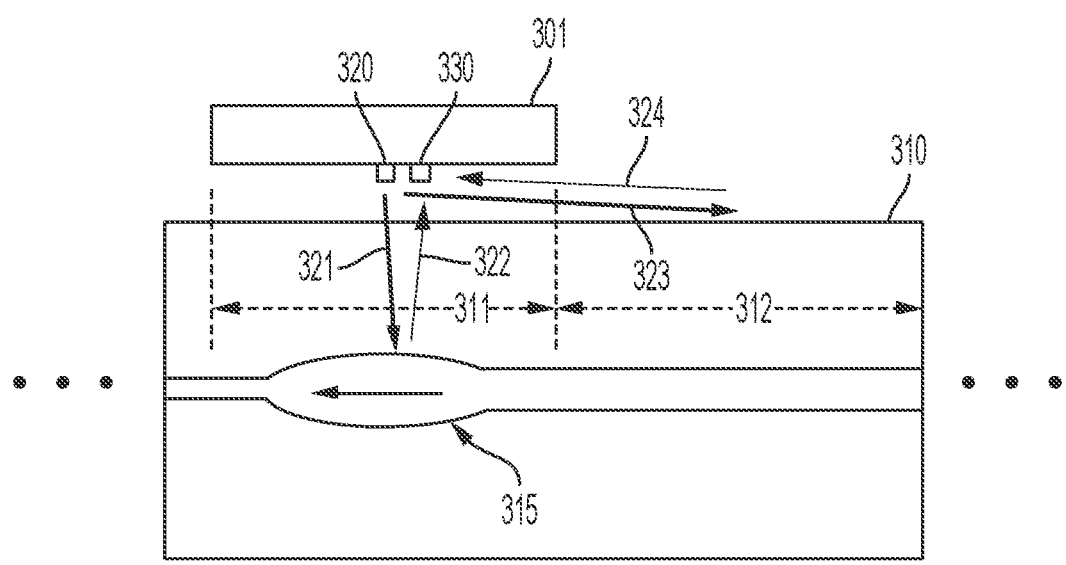
FIG. 3 illustrates a cross-section side-view of a smart watch configured for photoplethysmography of a wrist of a user according to a possible implementation of the present disclosure.

FIG. 3 illustrates a cross-section side-view of a smart watch configured for photoplethysmography according to a possible implementation of the present disclosure. The smart watch 301 is proximate to a wrist 310 of a user. The smart watch 301 includes a light source 320 and a detector 330 for measuring a blood volume of a blood vessel 315.

The light source 320 (e.g., LED, LD, OLED, etc.) is configured to project focused-light 321 towards a first area 311 (i.e., first portion) of the wrist under the smart watch 301, while the detector 330 (e.g., photodiode) is configured to receive back-reflected light that includes a focused-light component 322 that is reflected back to the detector from a blood vessel 315 in the first area 311 of the wrist 310 under the smart watch 301.

While the light source 320 may be designed to project all transmitted light into the area under the smart watch, some of the transmitted light may be transmitted to a second area 312 (i.e., second portion) of the wrist that is adjacent to the smart watch (i.e., not under the smart watch). That the second area 312 is adjacent to the smart watch may relate to the second area 312 abutting the first area in a direction transversal to a direction along which the focused-light 321 is emitted. For example, due to reflection and/or refraction of objects in the path of the transmitted light, a stray-light component 323 of the transmitted light may propagate towards the surface of the wrist not under the smart watch 301. The stray-light component can be back-reflected to the detector when an object (e.g., a finger) is brought into contact with the second area 312 of the wrist. In other words, the detector may receive back-reflected light including a focused-light component 322 and a stray-light component 324. The focused-light component 322 may be modulated by blood flow, while the stray-light component 324 may be modulated by a touch to the second area 312 of the wrist not under the smart watch 301 (i.e., proximate to the smart watch).

It should be noted that the stray-light component 323 shown in FIG. 3 is one possible path for the stray light that appears in the second area 312 of the wrist and that various combinations of scattering, reflection, refraction, and other light generating phenomena may result in a stray-light component in the portion of the wrist not under the smart watch. Additionally, it should be noted that stray light in the second area 312 of the wrist may result from ambient light sources (not shown) having similar wavelengths as the transmitted light. For example, a room light may illuminate the second area 312 of the wrist at wavelengths similar (e.g., the same) as the transmitted light wavelength.

Just as increased blood volume in the area under the smart watch can change the intensity of the back reflected focused-light, a touch to the wrist can change the intensity of the back reflected stray-light. Accordingly, the detector may simultaneously measure both phenomena. A touch to the wrist may change (i.e., increase) an amount of light detected at the detector while the touch exists. Accordingly, a tap to the wrist may be detected as a pulse at the detector. Further, an intensity of the pulse may provide information regarding the location of the touch on the wrist.

Figure 4:
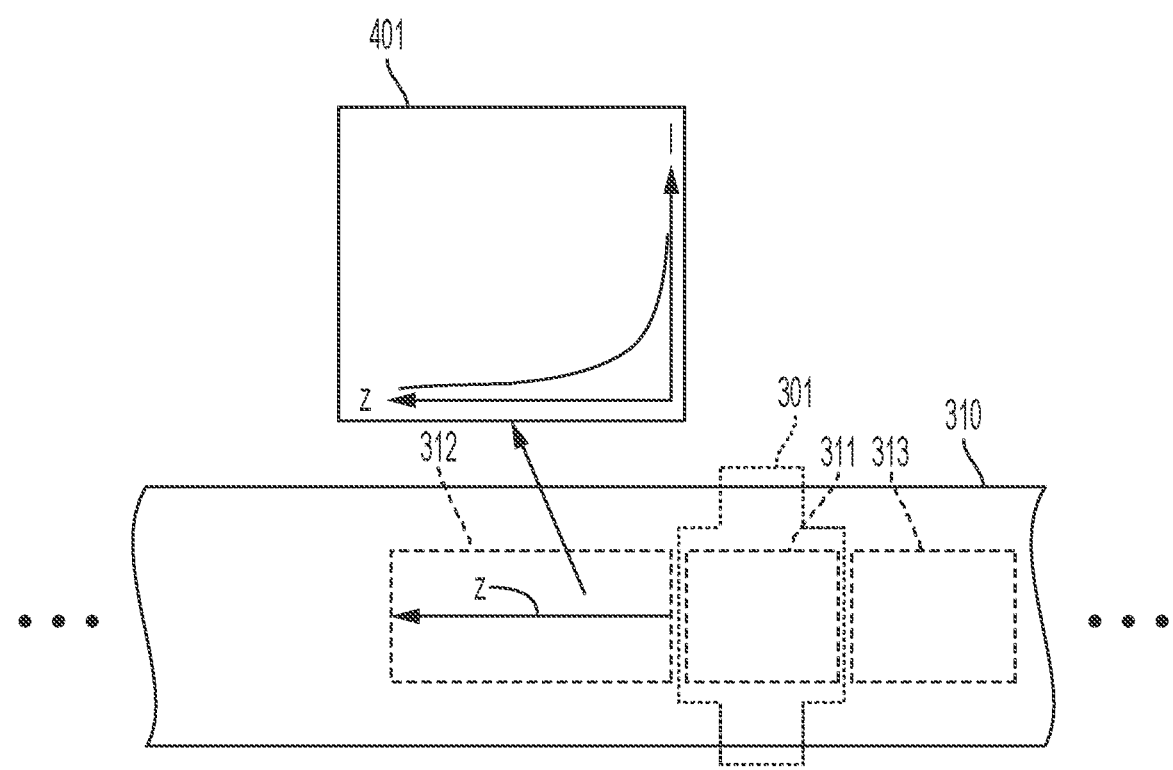
FIG. 4 illustrates a top-view of the smart watch shown in FIG. 3.

FIG. 4 illustrates a top-view of the smart watch shown in FIG. 3. The smart watch 301 is worn on the wrist 310 of a user. As described the PPG sensor of the smart watch 301 includes a light source configured to project transmitted light towards the wrist 310. The transmitted light includes focused light, which is projected to a first area 311 under the smart watch, and stray-light, which is projected to a second area 312 or a third area 313 not under the smart watch. In other words, the stray-light may leak from the light source to areas of the user adjacent to edges (e.g., edge facing the hand, edge facing the forearm) of the smart watch. For example, the stray-light light may leak onto the wrist, forearm, and/or hand (e.g., back of the hand) of the user. The intensity of the stray-light in the second area 312 or third area 313 may be low compared to the focused-light in the first area 311 for at least the reason that the leakage of light from the PPG sensor into the second area 312 or third area 313 may be unintentional. The intensity of the stray-light in the second area 312 or the third area 313 may not be uniform. For example, the stray light intensity in the second area 312 may decrease along a direction (z) moving away from the smart watch 301. An inset 401 to the figure illustrates a possible drop in stray-light intensity (I) starting at the smart watch 301 and moving along the wrist 310 away from the smart watch 301. The drop in intensity may be used to further characterize a gesture because light reflected from a touch closer to the smart watch 301 may be received at the detector 330 with a higher intensity than a light reflected from a touch further from the smart watch 301. While a smart watch is shown and described, it should be noted the present disclosure can be applied to other wearables worn on other parts of the body. For example, a wearable worn on a finger may apply the same technology to extend a touch interaction to surfaces of the user (e.g., hand) proximate to (i.e., around) the finger-worn wearable.

Figure 5:
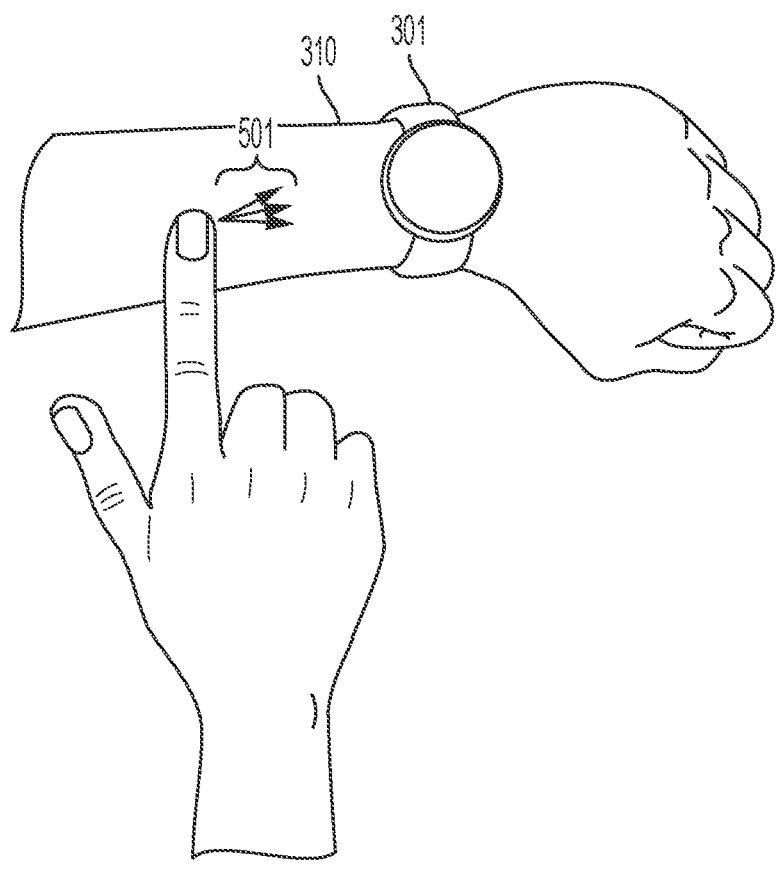
FIG. 5 illustrates a touch gesture to a wrist of a user wearing a smart watch according to a possible implementation of the present disclosure.

FIG. 5 illustrates a touch gesture (i.e., gesture) to a wrist of a user wearing a smart watch according to a possible implementation of the present disclosure. The gesture may produce reflected light 501 that can be received at the detector of a PPG sensor of the smart watch. The received light at the detector can include (i) a focused-light component that can be modulated (e.g., by blood flow) to include information about a heart rate and (ii) a stray-light component that can be modulated (e.g., by a touch) to include information about a gesture. The stray light component may be much smaller than the focused-light component and isolating the stray-light component to obtain information about the gesture may require filtering the received light.

Figure 6:
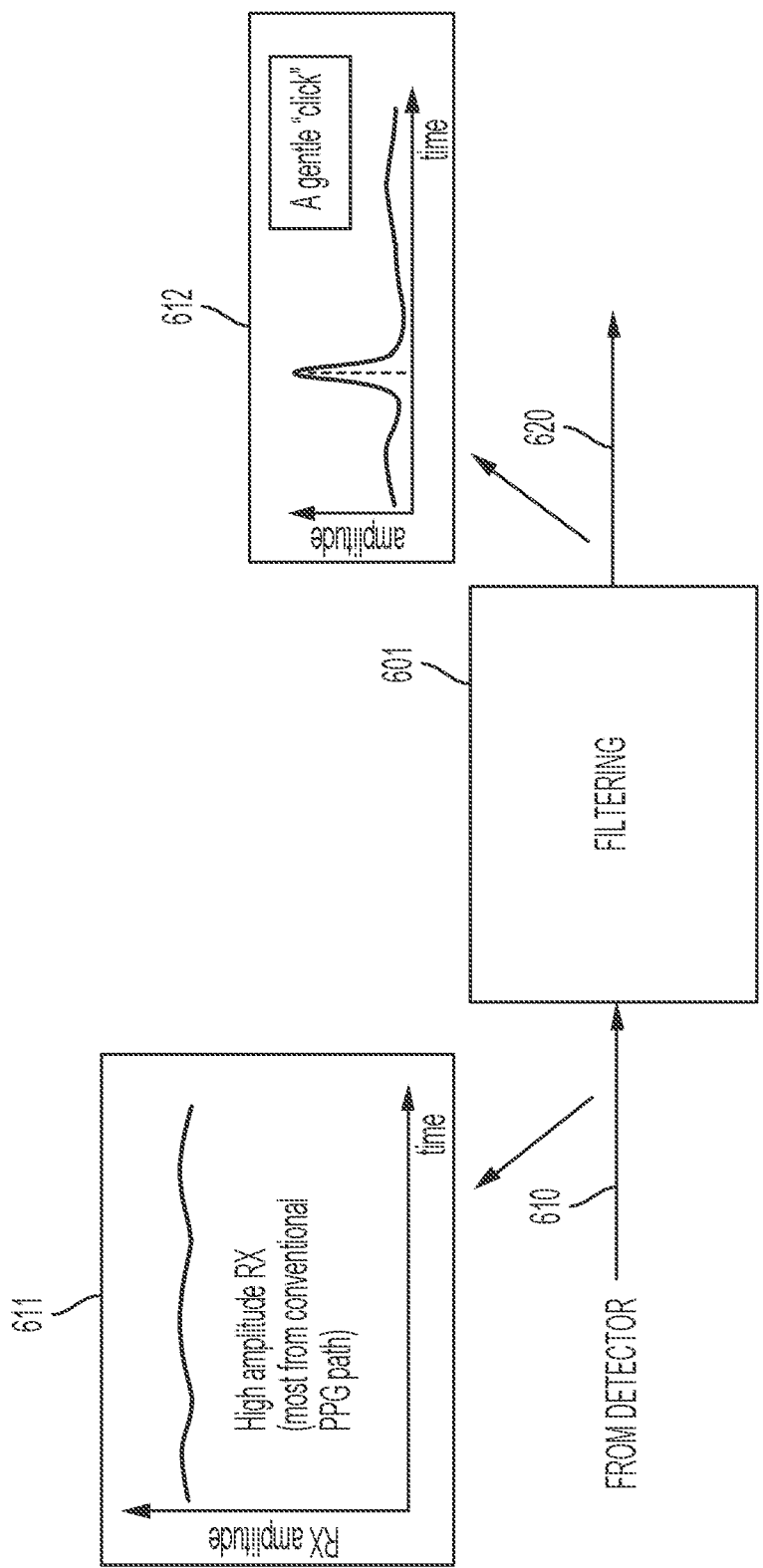
FIG. 6 illustrates a filtering block configured to isolate a stray-light component of back-reflected light according to a possible implementation of the present disclosure.

FIG. 6 illustrates a filtering block configured to isolate a stray-light component of back-reflected light. As shown, a first signal 611 corresponding to back-reflected light sensed by the detector is received at an input 610 of the filtering block 601 (i.e., filtering module). The first signal 611 corresponds to the total light received at the detector (i.e., RX(TOTAL)) and includes a focused-light component (i.e., RX(PPG)) corresponding to the heartbeat of a user and a stray-light component (i.e., RX(TOUCH)) corresponding to a gesture (e.g., single click) of a user, as described in the equation below.

$$RX(\text{TOTAL}) = RX(\text{PPG}) + RX(\text{TOUCH}) \quad (1)$$

The focused-light component may be much larger than the stray-light component (i.e., RX(PPG)>>RX(TOUCH)) so that a heartbeat may be observed in the first signal 611, but a touch gesture is not. The filtering block 601 is configured to generate a second signal 612 corresponding to the stray-light component from the first signal 611. The touch gesture may be observed in the second signal.

The filtering block 601, may exploit the time/frequency differences of a heartbeat signal and a touch gesture to filter the back-reflected light to isolate a stray-light component. For example, a typical heartbeat signal may change slowly in time at a relatively fixed frequency (e.g., 60 to 180 cycles per minute), which corresponds to a narrowband frequency response. Conversely, a touch gesture may change more quickly in time and have a broader frequency response than the heartbeat signal. These characteristics may be used to separate the signals.

In a possible implementation, the filtering block 601 may include time-domain processing such as principal component analysis (i.e., PCA), which assumes that the received light includes a slower varying component (e.g., heartbeat) and a faster varying component (e.g., gesture) in order to determine the principal components of the received signal.

In a possible implementation, filtering the back-reflected light to isolate a stray-light component may include performing principal component analysis on the back-reflected light to determine the focused-light component, then subtracting the focused-light component from the back-reflected light to isolate the stray-light component.

In another possible implementation, the filtering block 601 may include frequency domain processing such as notch filtering or low-pass filtering to remove frequencies likely produced by the heartbeat signal from the total received light. After filtering the second signal 612 corresponding to the stray light component may be processed to generate a waterfall image.

Figure 7:
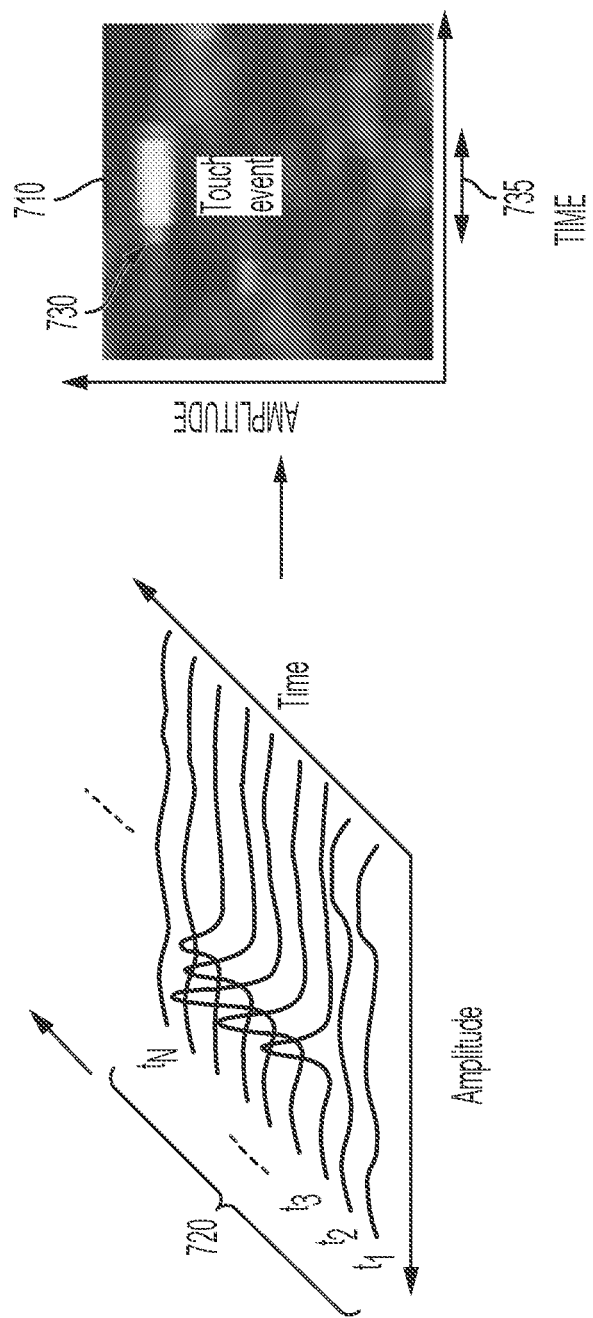
FIG. 7 illustrates a process to generate a waterfall image according to a possible implementation of the present disclosure.

FIG. 7 illustrates a process to generate a waterfall image according to a possible implementation of the present disclosure. The waterfall image 710 is a two-dimensional image that represents possible amplitudes (i.e., intensities) of the reflected light measured at intervals (i.e., time samples) during a window of time. Accordingly, the pixels of the waterfall image may have pixel values that represent the amplitudes (e.g., likelihood of amplitudes) of the stray light at times within the window. The process to generate the waterfall image can include gathering time samples ($t_1, t_2, t_3, \ldots t_N$) of the output 620 of the filtering block 601. The time samples may be gathered continuously, and a sliding window 720 may select a set of the time samples for a waterfall image. As shown, a collection (i.e., set) of time sampled amplitudes is converted to a waterfall image 710. Converting the detector data into a waterfall image may advantageously allow for image processing techniques to be used to determine a touch event.

As shown in FIG. 7, a touch event 730 (i.e., touch gesture) may appear as a bright spot in the waterfall image 710. A time-length 735 of the touch event in the waterfall image 710 (i.e., a time interval 735 on the abscissa over which the touch event extends in the waterfall image 710) may correspond to a duration of the touch event. For example, a touch event with a long time-length may be a long-touch (e.g., touch and hold) gesture, while a touch event with a short time-length may be a short-touch (e.g., click) gesture. A location of the touch event on the amplitude axis may correspond to a location of the touch gesture on the wrist (see FIG. 4). For example, a touch event aligned with a larger amplitude may be considered to have occurred closer to the watch than a touch event aligned with a smaller amplitude. Accordingly, different touch gestures may each have a characteristic waterfall image.

Figure 8:
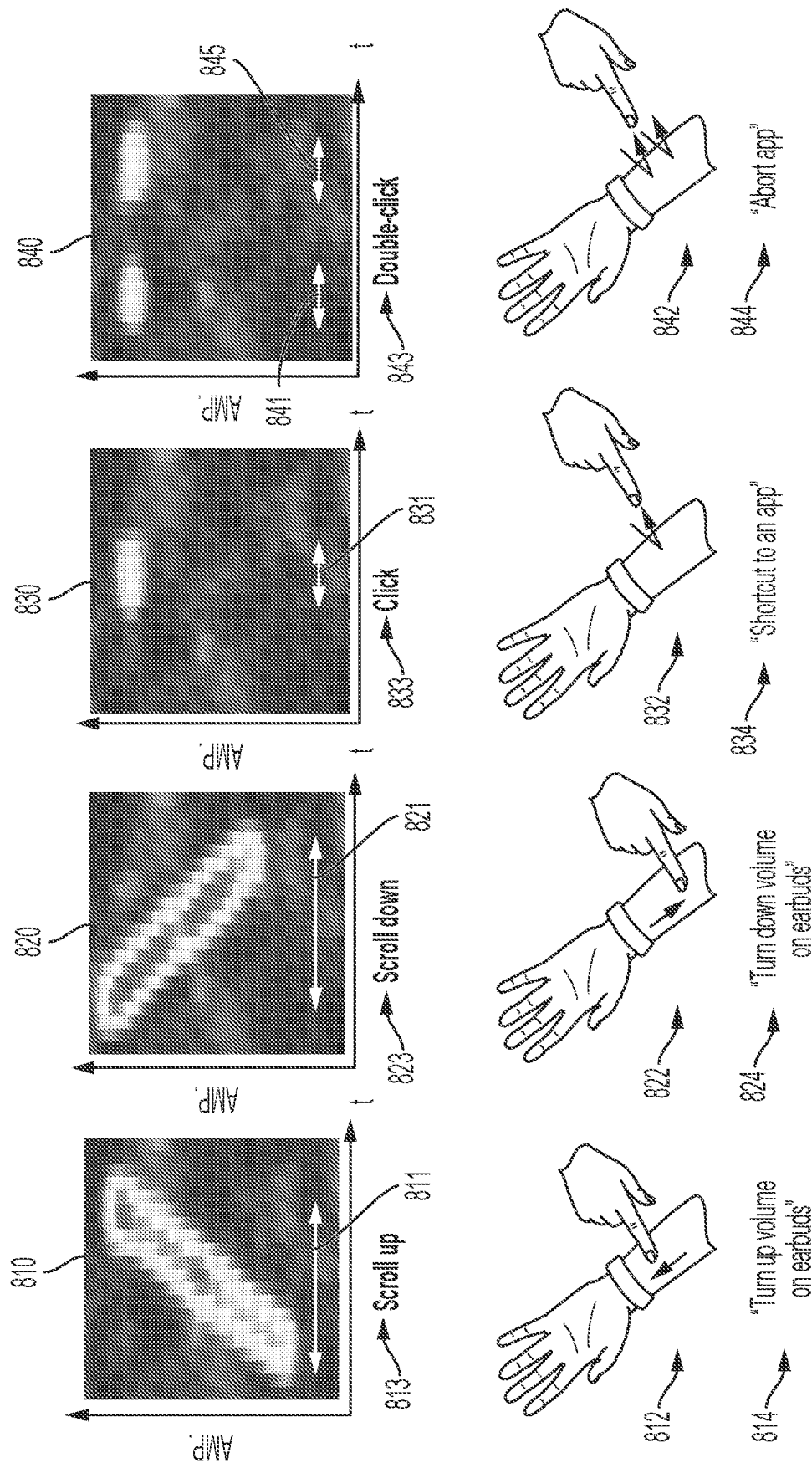
FIG. 8 illustrates possible waterfall images corresponding to gestures according to possible implementations of the present disclosure.

FIG. 8 illustrates possible waterfall images corresponding to gestures. In a first waterfall image 810, a first touch event (i.e., bright stripe) has a longer time-length 811 (e.g., than a click) and increases from a lower amplitude to a higher amplitude over time (i.e., has a positive slope). The first touch event with these characteristics may correspond to a first touch gesture 812 that includes a finger sliding on the wrist towards the smart watch. This first touch gesture having a bright stripe extending in time from a relatively low-amplitude (i.e., low amplitude) to a relatively high-amplitude (i.e., high amplitude) may be recognized (e.g., classified) as a scroll-up gesture 813. The scroll-up gesture may be interpreted by an application running on the smart watch as a first command 814. This application may, in turn, control a device communicatively coupled to the smart watch. For example, a scroll-up gesture may control the smart watch to "turn up a volume on earbuds coupled to the smart watch."

In a second waterfall image 820, a second touch event (i.e., bright stripe) has a longer time-length 821 (e.g., than a click) and decreases from a higher amplitude to a lower amplitude over time (i.e., has a negative slope). The second touch event with these characteristics may correspond to a second touch gesture 822 that includes a finger sliding on the wrist away from the smart watch. This second touch gesture having a bright stripe extending in time from a relatively high amplitude (i.e., high amplitude) to a relatively low amplitude (i.e., low amplitude) may be recognized (e.g., classified) as a scroll-down gesture 823. The scroll-down gesture may be interpreted by an application running on the smart watch as a second command 824. For example, a scroll-down gesture may control the smart watch to "turn down a volume on earbuds coupled to the smart watch."

In a third waterfall image 830, a third touch event (i.e., single bright spot) has a shorter time-length 831 (e.g., than a scroll) and remains at one amplitude (i.e., has a zero slope). The third touch event with these characteristics may correspond to a third touch gesture 832 that includes a finger tap to the wrist at some distance from the smart watch. This third touch gesture having a single bright spot in the waterfall image may be recognized (e.g., classified) as a single click gesture 833. The single-click gesture may be interpreted by an application running on the smart watch as a third command 834. For example, a single-click gesture may control the smart watch to "shortcut to an app."

In a fourth waterfall image 840, a fourth touch event (i.e., two bright spots) has a first-time length 841 and a second-time length 845 that are each of a shorter (e.g., than a scroll) duration. Each of the bright spots remains at one amplitude (i.e., has a zero slope), and in this example, each of the bright spots has the same amplitude. The fourth touch event with these characteristics may correspond to a fourth touch gesture 842 that includes a finger double-tapping the wrist at some distance from the smart watch. This fourth touch gesture having two bright spots in the waterfall image may be classified as a double-click gesture 843. The double click gesture may be interpreted by an application running on the smart watch as a fourth command 844. For example, a double-tap gesture may control the smart watch to "abort app."

A sliding window applied to the signals received from the detector(s) of the PPG sensor may generate a set (i.e., sequence, stream) of waterfall images. In other words, subsequent waterfall images may be iterations of a sliding window applied to the stray-light component of the back-reflected light. Each waterfall image may be analyzed (e.g., in sequence) to detect a touch event (i.e., touch). If a touch is detected in a waterfall image, the waterfall image may be applied (i.e., routed) to a gesture classifier which can be configured to identify a gesture corresponding to the touch. If a touch is not detected in the waterfall image, identifying the gesture may be unnecessary. Accordingly, if a touch is not detected in the waterfall image, the waterfall image may not be routed to the gesture classifier. In other words, the process may move to the next waterfall image in the sequence without performing the classification on the (no touch) waterfall image. This optional classification may advantageously conserve processing resources and/or power consumption (i.e., power). In a possible implementation, images without a detected touch may be discarded (e.g., to conserve memory).

Figure 9:
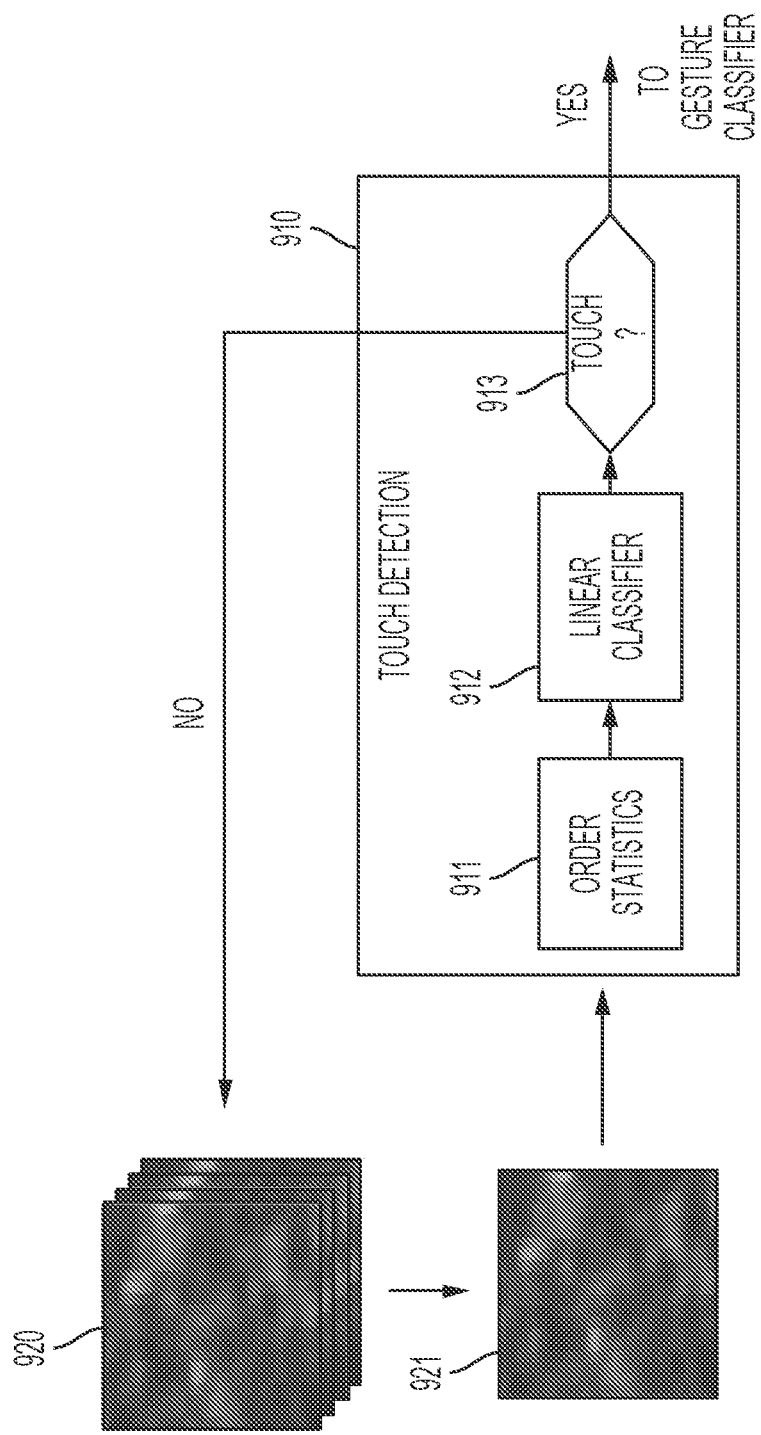
FIG. 9 illustrates a process for analyzing waterfall images to detect a touch according to a possible implementation of the present disclosure.

FIG. 9 illustrates a process for analyzing waterfall images to detect a touch according to a possible implementation of the present disclosure. A waterfall image 921 is selected from a set of waterfall images 920. The waterfall image 921 is then applied to a process for touch detection block 910 that is configured to determine if a touch is present in the waterfall image 921. The touch detection block 910 may be configured to determine order statistics 911 of the waterfall image (W). The order statistics may include a maximum pixel value (i.e., max(W)) and a minimum pixel value (i.e., min(W)). The touch detection block may be further configured to apply the order statistics to a touch classifier (i.e., linear classifier).

Figure 10:
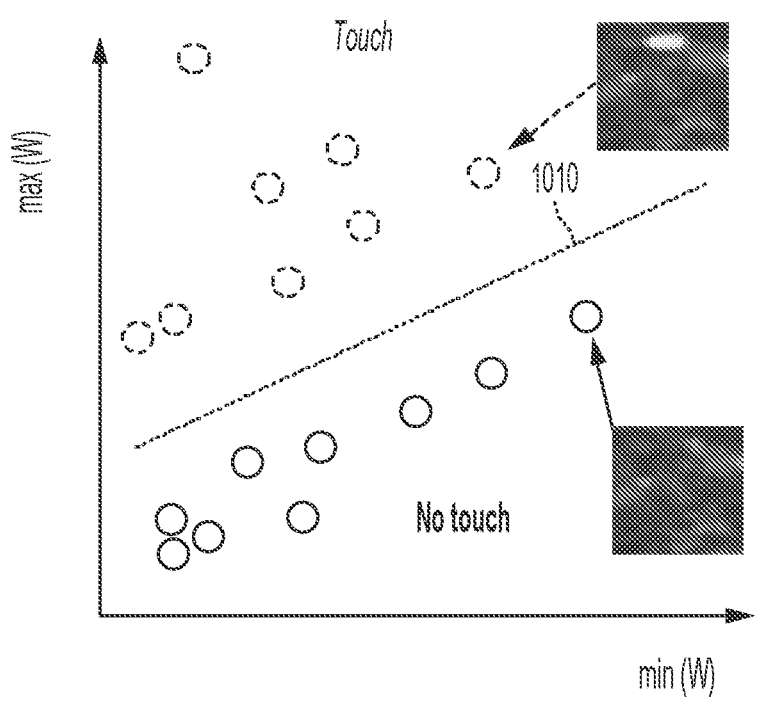
FIG. 10 illustrates support vector machine (SVM) training for touch detection according to an implementation of the present disclosure.

The linear classifier can be trained based on a support vector machine (SVM) protocol. FIG. 10 illustrates details of the SVM training for touch detection according to an implementation of the present disclosure. As shown, a collection of waterfall images are analyzed and the max(W) and min(W) for each image are plotted according to a max dimension and a min dimension. When the order statistics are plotted for a set of training waterfall images, the training waterfall images with a touch present form a group above a line and the training waterfall images with no touch present form a group below the line. The line is known as a hyperplane 1010 and is the basis for determining a probability of touch being present in a waterfall.

Returning to FIG. 9, the linear classifier 912 can estimate a probability of a touch being present in the waterfall image (i.e., $p_{SVM}$) from the order statistics, as shown in the equation below for a touch probability.

$$p_{SVM} = \sigma(a_1 \cdot \max(W) + a_2 \cdot \min(W) + b) \quad (2)$$

In the equation above $a_1$, $a_2$, and b are SVM coefficients obtained from machine learning (i.e., training) on training waterfall images, as shown in FIG. 10. In the equation above, σ is a sigmoid operator that fits an infinite amplitude range into fixed range (e.g., $0 \le p_{SVM} \le 1$) corresponding to a probability. The probability ($p_{SVM}$) may be compared to a threshold to decide 913 if the waterfall image includes a touch (YES) or no touch (NO). When the touch is determined (i.e., YES), the waterfall image may be routed to a gesture classifier configured to recognize a pattern in the waterfall image as a touch gesture (i.e., touch). Otherwise (i.e., NO), the process may iterate to the next waterfall image in the set of waterfall images 920.

Figure 11:
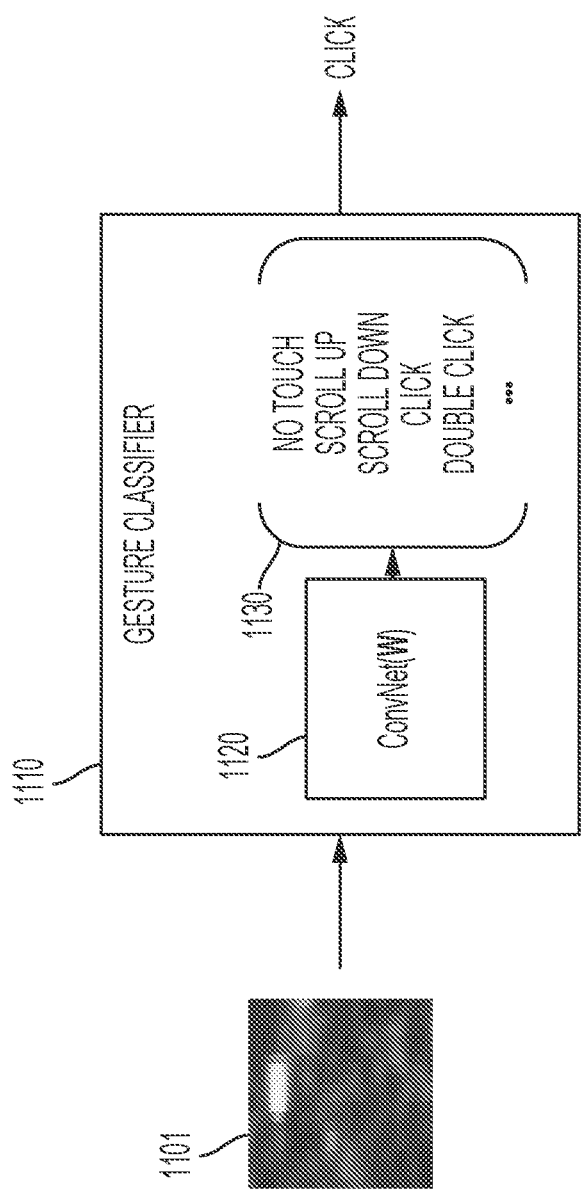
FIG. 11 illustrates a process for identifying a gesture in a waterfall image according to a possible implementation of the present disclosure.

FIG. 11 illustrates a process for identifying a gesture in a waterfall image according to a possible implementation of the present disclosure. As shown, a waterfall image 1101 determined to have a touch is applied to a gesture classifier 1110. The gesture classifier may include a two-dimensional convolutional neural network (i.e., ConvNet(W)). The 2D convolutional neural network 1120 may have two convolutional layers followed by two fully connected layers and can include five interaction classes, with four being nontrivial. When the waterfall image 1101 is input, the convolutional neural network 1120 may generate weights (e.g., probabilities) at a plurality of outputs corresponding to a plurality of gestures 1130. In other words, the classifier is configured to recognize particular patterns in waterfall images as particular gestures and assign a high weight to the recognized gesture. In one possible implementation, the output with the highest weight may be recognized as the gesture. In another possible implementation, the output above a threshold may be recognized as the gesture. As shown in FIG. 11, the gestures may include NO TOUCH, SCROLL UP, SCROLL DOWN, CLICK and DOUBLE CLICK. For the example shown, the waterfall image 1101 causes the gesture classifier to output a click. This click may be used as a command to control an application.

Figure 12:
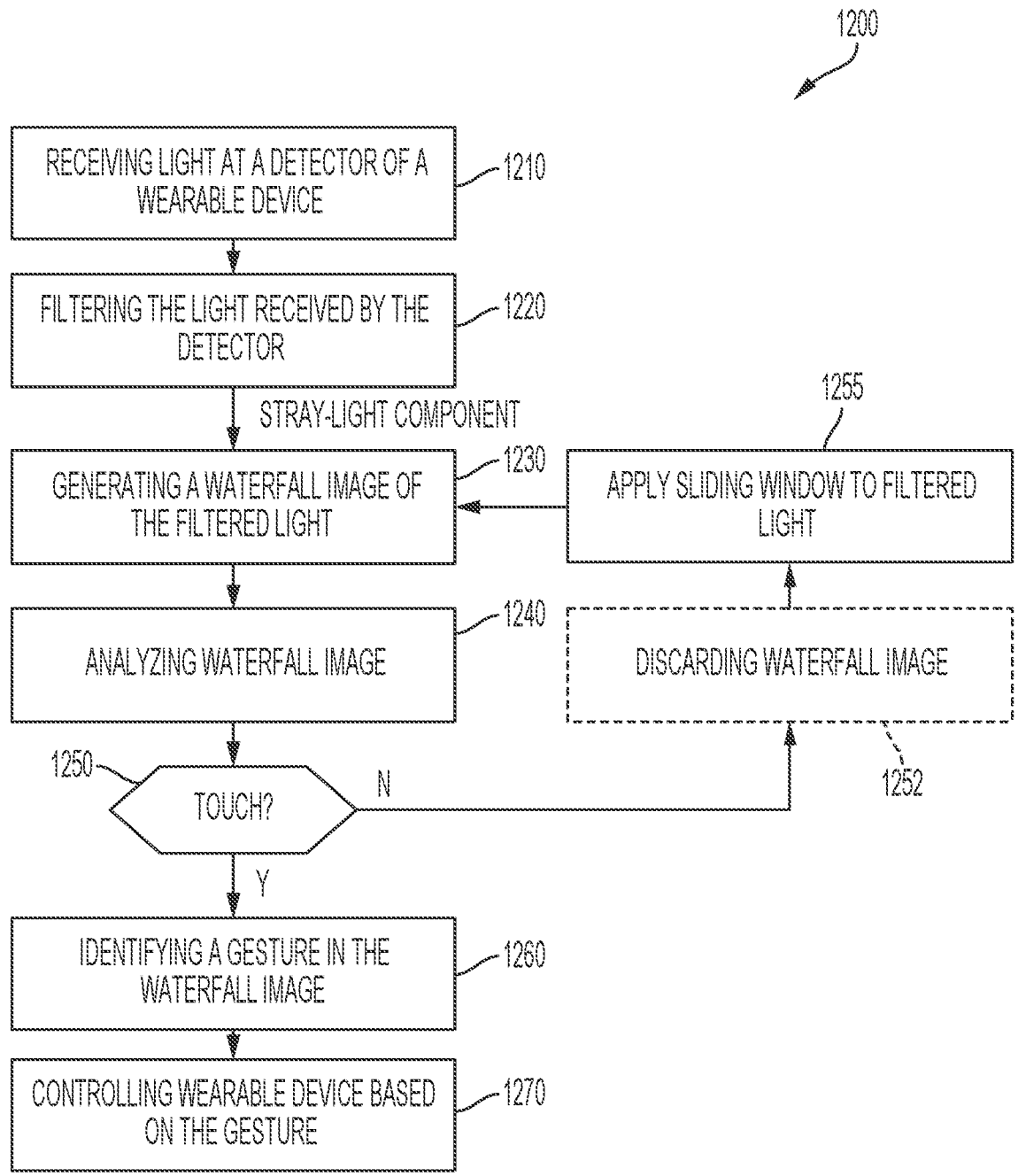
FIG. 12 is a flowchart of a method for controlling a wearable device according to a possible implementation of the present disclosure.

FIG. 12 is a flowchart of a method for controlling a wearable device according to a possible implementation of the present disclosure. The method 1200 includes receiving 1210 light at a detector of a wearable device. The detector described thus far has been a PPG detector (or detectors). In this implementation, the use of the detector for touch control adds a function to the PPG detector so that the PPG detector becomes dual-purposed, but other implementations are possible. For example, the detector may be a single-purposed detector added to the wearable device for touch control. Likewise, the light received at the detector may be part of a PPG light source or may be from a light source used for the purpose of touch control. In these implementations, the light from the light source may be directed to a body area (e.g., wrist, forearm) used for touch control rather than directed to the body area below (i.e., under, covered by, etc.) the wearable device.

The method 1200 further includes filtering 1220 the light received by the detector. The filtering can isolate the received light so that a change caused by a touch is observable even when other (e.g., higher intensity) light is received at the detector. This filtering may include filtering based on principal component analysis or frequency domain filtering. For the implementation of the smart watch, the filtering isolates a stray-light component from the received light at a PPG detector of a smart watch.

The method 1200 further includes generating 1230 a waterfall image of the filtered light. The waterfall image is a two-dimensional image that includes information about the time of a gesture on a first axis and information about the intensity (i.e., amplitude) of a gesture on a second axis. Accordingly, a number of touches (e.g., during a window of time) can be determined (i.e., detected). Further, because the intensity can be correlated with a touch position, a change in position during a touch can also be detected.

The method 1200 further includes analyzing 1240 the waterfall image. A waterfall image that includes a touch may have a condition that includes a brighter area of pixels within an area of darker pixels. Accordingly, a variety of image analysis techniques can be used to determine this condition. One possible technique includes a linear classifier based on a maximum pixel value and a minimum pixel value of a waterfall image. The linear classifier is trained (e.g., prior to use and/or at intervals) using a variety of training images that include a touch and a variety of images that do not include a touch. The training can utilize a support vector machine to determine a criterion to distinguish the waterfall image as including a touch or not including a touch.

The method 1200 further includes deciding 1250 if the waterfall image includes a touch. If the waterfall image includes a touch (i.e., TOUCH?=Y), then the method 1200 includes identifying 1260 a gesture in the waterfall image. The identifying can use a gesture classifier that includes a neural network (e.g., 2D convolutional neural network). The neural network may be configured to receive the waterfall image at an input. The neural network may be configured to have a plurality of outputs, each corresponding to a gesture (e.g., including no-gesture). In operation, a waterfall image including a particular gesture may change an amplitude (e.g., increase an amplitude) on a particular output corresponding to the particular gesture to identify the gesture. After the gesture is identified, the method 1200 may include controlling 1270 the wearable device based on the gesture. For example, the gesture may control an application running on the wearable device.

If the waterfall image does not include a touch (i.e., TOUCH?=N), then the method 1200 includes obtaining a new waterfall image and repeating the process. The new waterfall image may be generated by applying 1255 a sliding window to the filtered light. In operation, the filtered light may be a continuous signal stream to which a sliding window may be applied to generate a sequence of waterfall images and generating the waterfall image can include using a next waterfall image in the sequence of waterfall images. In a possible implementation repeating the process includes discarding 1252 the waterfall image without the touch.

Figure 13:
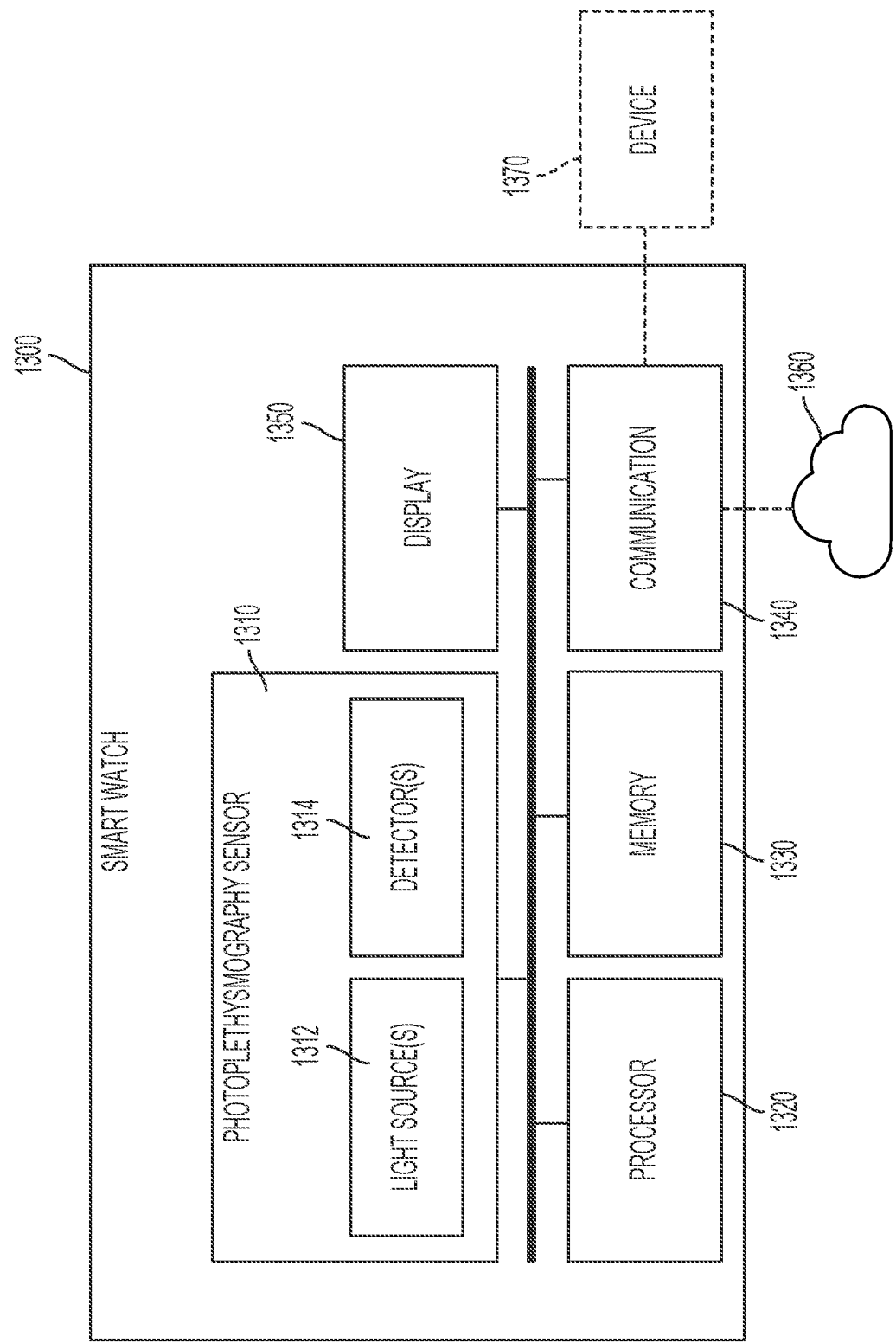
FIG. 13 is a block diagram of a smart watch according to a possible implementation of the present disclosure.

FIG. 13 is a block diagram of a smart watch according to a possible implementation of the present disclosure. The smart watch 1300 can include a photoplethysmography sensor 1310 that includes one or more light sources 1312 and one or more detectors 1314. Each light source can be configured to project transmitted light. The transmitted light can include light focused on a portion of a wrist under the smart watch and light that leaks to a portion of the wrist not under the smart watch. Each detector can be configured to receive back-reflected light. The back-reflected light can include back-reflected light from the portion of a wrist under the smart watch and back-reflected light from the portion of the wrist not under the smart watch.

The smart watch further includes at least one processor 1320. The processor can be configured by software instructions to execute a process for identifying a gesture from the back-reflected light from the portion of the wrist not under the smart watch. The software instructions may be stored in (and recalled from) a memory 1330. Additionally, information related to the process (e.g., waterfall images, classifiers, etc.) may be stored and recalled from the memory 1330. The memory 1330 may be a non-transitory computer readable memory, such as a solid-state drive (SSD). In some implementations, the processing and/or memory may be supplemented or replaced by a processor or a memory of a remote device. Accordingly, the smart watch 1300 may further include a communication module 1340 configured to transmit and receive information with remote devices via a communication link (e.g., WiFi, CDMA, etc.). In a possible implementation, the storage and/or processing for gesture detection and recognition may be carried out via a remote network of computers/memory devices (i.e., cloud computer network 1360). In another possible implementation, the smart watch may be coupled (e.g., via Bluetooth, UWB) to a device 1370 (e.g., earbuds) and the touch gesture may control the device.

The smart watch 1300 may further include a display 1350 (e.g., touch display) that is configured to present information and receive touch gestures. The gesture detection and recognition described thus far may duplicate, supplement, or replace the touch features of the display 1350. The gestures recognized by the display or by the wrist may control the smart watch 1300.

While certain features of the described implementations have been illustrated as described herein, many modifications, substitutions, changes and equivalents will now occur to those skilled in the art. For example, a smart watch may be worn on a wrist in different configurations, thereby changing portions of the wrist/forearm that can be used for applying a touch. It is, therefore, to be understood that the appended claims are intended to cover all such modifications and changes as falling within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used in this specification, a singular form may, unless definitely indicating a particular case in terms of the context, include a plural form. Spatially relative terms (e.g., over, above, upper, under, beneath, below, lower, and so forth) are intended to encompass different orientations of the device in use or operation in addition to the orientation depicted in the figures. In some implementations, the relative terms above and below can, respectively, include vertically above and vertically below. In some implementations, the term adjacent can include laterally adjacent to or horizontally adjacent to.

The invention claimed is:

1. A method for controlling a wearable device, the method comprising:
   transmitting light from a light source of a sensor of the wearable device when the wearable device is worn on a skin surface, the light including:
      a first light component that is transmitted towards a first area of the skin surface covered by the wearable device; and
      a second light component that is transmitted towards a second area of the skin surface that is not covered by the wearable device;
   receiving back-reflected light at a detector on the sensor, the back-reflected light including a focused-light component from the first area and a stray-light component from the second area;
   filtering the back-reflected light to isolate the stray-light component, the filtering based on the first light component being in a relatively low frequency band with respect to the second light component; and
   analyzing the stray-light component to detect a touch in the second area.

2. A wearable device comprising:
   a sensor including:
      a light source configured to project transmitted light towards a portion of a wearer under the wearable device and towards a portion of the wearer not under the wearable device; and
      a detector configured to receive back-reflected light including a focused-light component that is reflected back to the detector from the portion of the wearer under the wearable device and a stray-light component that is reflected back to the detector from the portion of the wearer not under the wearable device; and
   at least one processor configured by software instructions to:
      filter the back-reflected light to isolate the stray-light component;
      generate an image of the stray-light component, the image having a first dimension corresponding to amplitudes of the stray-light component and a second dimension corresponding to a window of time; and
      analyze the image to detect a touch.

3. The wearable device according to claim 2, wherein the at least one processor is further configured by software to:
   recognize a pattern in the image as a gesture; and
   control the wearable device according to the gesture.

4. The wearable device according to claim 3, wherein the software instructions include a gesture classifier that is configured to recognize different types of gestures.

5. The wearable device according to claim 4, wherein the gesture classifier is configured to:
   recognize a single bright spot in the image as a single-click gesture;

recognize two bright spots in the image as a double-click gesture;

recognize a bright stripe extending in time from a higher amplitude of the image to a lower amplitude of the image as a scroll-down gesture; and recognize a bright stripe extending in time from the lower amplitude of the image to the higher amplitude of the image as a scroll-up gesture.

6. The wearable device according to claim 2, wherein to filter the back-reflected light to isolate the stray-light component; the at least one processor is configured to:

perform principal component analysis on the back-reflected light to determine the focused-light component as having principal components that vary with a frequencies corresponding to a range of heart beat frequencies; and subtract the focused-light component from the back-reflected light to isolate the stray-light component.

7. The wearable device according to claim 2, wherein to analyze the image to detect a touch in the image; the at least one processor is configured to:

classify the image as having a touch or not having a touch based on a maximum pixel value of the image.

8. A smart watch comprising:

a sensor including:

a light source configured to project transmitted light towards a portion of a wrist under the smart watch and towards a skin surface of the wrist not under the smart watch; and a detector configured to receive back-reflected light from the skin surface of the wrist not under the smart watch; and at least one processor configured by software instructions to:

generate an image of the back-reflected light, the image having pixel values corresponding to amplitudes of the back-reflected light measured during a first window of time;

analyze the image to detect a touch to the portion of the wrist not under the smart watch;

identify a pattern in the image as a gesture when the touch is detected; and control the smart watch based on the gesture.

9. The smart watch according to claim 8, wherein the at least one processor is further configured by the software instructions to:

filter the back-reflected light so that the touch is visible in the image.

10. The smart watch according to claim 8, wherein control the smart watch based on the gesture includes controlling a device coupled to the smart watch.

11. The method according to claim 1, further comprising:

generating an image of the stray-light component, the image having pixel values in a first dimension corresponding to amplitudes of the stray-light component reflected from the second area and a second dimension corresponding to a window-of-time;

analyzing the image to detect the touch in the second area;

responsive to detecting the touch, identifying a pattern in the image corresponding to how the amplitudes of the stray-light component changes during the window-of-time;

determining a gesture based on the pattern in the image; and controlling the wearable device based on the gesture.

12. The method according to claim 11, wherein filtering the back-reflected light to isolate the stray-light component includes:

performing principal component analysis on the back-reflected light to isolate the stray-light component based on the focused-light component having principal components that vary according to a heart beat.

13. The method according to claim 11, wherein the analyzing the image to detect the touch in the second area includes:

determining a maximum pixel value and a minimum pixel value;

obtaining a touch probability based on the maximum pixel value and the minimum pixel value; and determining that the touch occurred during the window-of-time or that no touch occurred during the window-of-time based on the touch probability.

14. The method according to claim 11, wherein determining the gesture based on the pattern in the image includes:

determining a single-click gesture based on a single bright spot in the image.

15. The method according to claim 11, wherein determining the gesture based on the pattern in the image includes:

determining a double-click gesture based on a two bright spots in the image.

16. The method according to claim 11, wherein determining the gesture based on the pattern in the image includes:

determining a scroll-down gesture based on a bright stripe extending from a higher amplitude to a lower amplitude during the window-of-time in the image.

17. The method according to claim 11, wherein determining the gesture based on the pattern in the image includes:

determining a scroll-up gesture based on a bright stripe extending from a lower amplitude to a higher amplitude during the window-of-time in the image.

18. The method according to claim 11, wherein the wearable device is a smart watch.

19. The method according to claim 18, wherein the sensor is a photoplethysmography sensor directed towards a wrist of a user wearing the smart watch.

* * * * *